United States Patent
Macher et al.

(10) Patent No.: US 8,664,571 B2
(45) Date of Patent: Mar. 4, 2014

(54) CLOTHING PIECE WITH HEATING DEVICE

(75) Inventors: David Macher, Oesterreich (AT); Gerhard Kremer, Oesterreich (AT); Urs Maron, Oesterreich (AT)

(73) Assignee: Sidas Central GmbH, Vienna (AT)

( * ) Notice: Subject to any disclaimer, the term of this patent is extended or adjusted under 35 U.S.C. 154(b) by 483 days.

(21) Appl. No.: 12/864,456

(22) PCT Filed: Jan. 26, 2009

(86) PCT No.: PCT/EP2009/000596
§ 371 (c)(1),
(2), (4) Date: Nov. 12, 2010

(87) PCT Pub. No.: WO2009/092618
PCT Pub. Date: Jul. 30, 2009

(65) Prior Publication Data
US 2011/0049117 A1 Mar. 3, 2011

(30) Foreign Application Priority Data

Jan. 25, 2008 (DE) .................. 10 2008 006 939

(51) Int. Cl.
*H05B 1/00* (2006.01)

(52) U.S. Cl.
USPC ........... 219/211; 219/494; 219/529; 219/548; 219/549

(58) Field of Classification Search
USPC ......... 219/211, 494, 523, 527–529, 545, 548, 219/549
See application file for complete search history.

(56) References Cited

U.S. PATENT DOCUMENTS

| | | | |
|---|---|---|---|
| 3,708,649 A * | 1/1973 | Crowley et al. | 219/212 |
| 6,239,410 B1 | 5/2001 | Tackore | |
| 6,649,873 B1 | 11/2003 | Cintron, Jr. et al. | |
| 7,307,242 B1 * | 12/2007 | Chen | 219/211 |

(Continued)

FOREIGN PATENT DOCUMENTS

| | | |
|---|---|---|
| DE | 2903898 | 8/1979 |
| DE | 19808851 A1 | 11/1998 |
| FR | 2645410 A | 10/1990 |
| JP | 04098718 A | 3/1992 |

OTHER PUBLICATIONS

International Search Report from PCT/EP2009/000596, dated Jun. 17, 2009 (3 pages).
Elektronik 22/2003, pp. 52-57.

(Continued)

*Primary Examiner* — Brian Jennison
(74) *Attorney, Agent, or Firm* — Michael Best & Friedrich LLP

(57) ABSTRACT

The object of the invention is a clothing piece, such as a glove, with a heating device, in particular for the warming and/or temperature control of a skin surface with deep-acting effect upon areas of a human body, comprising at least one heat transfer element, at least one connection for an energy supply device, at least one control field with an encapsulation and with at least one circuit board with an electrical control circuit for controlling the temperature of the heat transfer element and at least two switches for the manual adjustment of the temperature. The encapsulation comprises a chamber that holds the circuit board and a protruding edge that surrounds the chamber, wherein the edge is made of a flexible material. In addition, the switches are made up of at least two contact elements located on the inside of the encapsulation and at least two contact elements formed on the circuit board.

29 Claims, 5 Drawing Sheets

(56) References Cited

U.S. PATENT DOCUMENTS

| | | | |
|---|---|---|---|
| 2003/0232518 A1* | 12/2003 | Tsutsui | 439/67 |
| 2004/0164066 A1* | 8/2004 | Ford et al. | 219/211 |
| 2005/0155961 A1 | 7/2005 | Gilligan et al. | |
| 2006/0092624 A1 | 5/2006 | Park | |
| 2008/0130268 A1* | 6/2008 | Johnson et al. | 362/103 |
| 2008/0223844 A1* | 9/2008 | Cronn | 219/211 |

OTHER PUBLICATIONS

Bernard Schroth, "Normalverbrauchers neue Gewander," Elektronik 22/2003, pp. 52-57 (2003).

\* cited by examiner

CLOTHING PIECE WITH HEATING DEVICE

RELATED APPLICATIONS

This application is a national stage filing under 35 U.S.C. §371 of International Application No. PCT/EP2009/000596, filed Jan. 26, 2009, which claims priority to German patent application number 10 2008 006 939.6, filed on Jan. 25, 2008. The contents of these applications are hereby incorporated by reference.

FIELD OF THE INVENTION

The subject of the invention is a garment according to the features of the preamble of claim 1.

BACKGROUND OF THE INVENTION

Heating devices, in particular for heating and/or temperature-control of a skin surface with a deep effect on partial regions of a human body, having at least one heat transfer element and at least one terminal for an energy supply device and also a control panel with an encapsulation are known in prior art. Thus for example the publication DE 198 08 851 A1 shows such a heating device.

The disadvantage of the heating device shown therein is that the control panel can be inserted only with difficulty in a glove or in a garment since, on the one hand, it has too great a spatial extension and the control panel must be disposed in a pocket secured externally on e.g. the glove. As a result, the operability is also impaired inter alia since a wearer of the gloves must firstly open the pocket and only then can access the control panel.

Fixed positioning of the control panel is not possible.

A further example of a garment, in this case a glove, with a heating device is shown for example in US 2005/0155961 A1. The control panel is also concealed hereby behind a Velcro fastener.

A garment with an integrated control panel is known from "Elektronik 22/2003, pp. 52-57". However direct sewing between the electronics and the garment is undertaken here so that only when the garment is completely finished can it be tested as to whether the control panel is functioning. If this is not the case, the garment must be undone again, which is associated with high additional costs.

A further example of a glove connected to a control panel can be deduced from US 2006/0092624 A1. However, it is disadvantageous here that the control panel is not connected integrally to the glove and, consequently, greater focus must be placed on the connection mechanism.

SUMMARY OF THE INVENTION

It is an object of the present invention to produce a garment with a heating device which can be operated simply and conveniently, can be of a small constructional size and can be inserted easily into a garment or the like. The object is achieved with a garment having the features of claim 1. Advantageous developments are described in the dependent claims.

Since the heating device of the garment has an encapsulation with a chamber receiving the circuit board and a flange-like edge surrounding the chamber, the circuit board with the electronics and electrics situated thereon is protected, on the one hand. The circuit board is thereby disposed within the chamber and cannot slip out of the chamber because of the at least partially closed edge which is present. A heating device of this type can be integrated easily in a garment with the flange-like edge surrounding the chamber. The flange-like edge which consists of a flexible material is thereby connected to the outer casing of the garment. An additional pocket for receiving the control panel is consequently unnecessary. Furthermore, the control panel can be connected frictionally to the garment without endangering the circuit board since this is disposed on its own in the chamber.

As a result of the fact that the at least one switch for manual adjustment of the temperature, preferably two switches, one for increasing and one for reducing the temperature, are formed respectively by one or two contact element(s) which are disposed on an inside of the encapsulation, and one or two contact elements which are configured on the circuit board, the switches can be produced, in a space-saving manner, from a combination of the encapsulation and the circuit board.

Consequently, no further wiring between a switch and the circuit board is necessary: the circuit board becomes part of the switch. Furthermore, it is consequently possible to configure the control panel to be very small, which simplifies in addition integration into the garment, such as, for example, a glove.

The encapsulation includes a plastic material. As a result, the encapsulation can be designed to be water-tight so that the circuit board disposed in the chamber is optimally protected.

The heating device is preferably produced and tested independently of the garment and before connection to the same. Subsequently, the encapsulation is disposed for example in a recess of the garment in such a manner that the chamber is situated preferably directly accessible in the recess and the flange-like edge is connected to the edge of the recess, for example by sewing or gluing.

As a result of the fact that the connection between the encapsulation and the garment is produced via the flange-like edge, there is no danger that the circuit board is damaged during connection.

The invention is explained subsequently by the example of a glove, the garments also being able to be a jacket, trousers or stockings.

A glove according to the invention has an outer casing and a heating device, as described above, the flange-like edge of the encapsulation being connected in the region of the back of a hand to the outer casing, preferably being sewn. As a result of the fact that the circuit board need have merely a small dimension (for example an area between 1 to 8 cm$^2$) and must be protected from blows or bending, the arrangement of the circuit board on the virtually flat back of a hand is suitable: the back of the hand in addition represents a hard flat base for the circuit board and protects the latter from damage. The back of the hand is essentially the only part of a hand, the surface of which remains constant during virtually all hand movements. The geometric changes because of muscle and bone movements are marginal in comparison with other hand surfaces. Furthermore, the circuit board is protected in addition by the encapsulation.

In one embodiment of the heating device, the encapsulation is produced from silicone or has silicone in large part. Silicone is advantageous since it is water-impermeable, can be glued well to many materials, is flexible and, on the other hand, can be sewn. Such an encapsulation can be processed readily and can be integrated advantageously subsequently into the glove. The plastic material can however also consist of materials such as rubber or PE.

In a further variant, the encapsulation is produced from an upper and a lower part, the chamber being formed between the upper and lower part and the upper and the lower part being connected to each other at their respective edge, preferably glued or welded, and thus forming the flange-like edge of the encapsulation. In this way, the circuit board can be inserted into the encapsulation in a particularly simple manner and the encapsulation can only be closed subsequently. This simplifies the production of the control panel.

In a further variant of the heating device, the encapsulation has at least one opening for guiding through a connection between the circuit board and the at least one heat transfer element and/or the at least one terminal. The opening is thereby chosen such that the latter is guided externally only in the flange-like edge region of the encapsulation. In this way, the chamber itself is prevented from having an opening through which moisture can have direct access to the circuit board. This improves the mode of operation of the heating device since moisture no longer has access to the circuit board. This is possible since the edge either has a thickness which is thicker than the width or thickness of a connection between the circuit board and the at least one heat transfer element and/or the at least one terminal or the opening extends in the edge region between an upper and a lower part of the encapsulation.

In a further variant, the encapsulation has support elements which protrude on the inside and are connected to the circuit board. It is possible via the support elements to ensure a spacing between the encapsulation and the electrical and electronic component s on the circuit board in the normal case. The normal case should hereby be understood such that no force acts on the chamber from outside. The support elements contribute in addition to the fact that the encapsulation cannot be pressed completely onto the circuit board.

In a further variant, at least two operating elements are disposed on the outside of the encapsulation, which operating elements are situated above the at least two contact elements which are disposed on the inside of the encapsulation so that a pressure applied on one of the two operating elements actuates the switch situated thereunder. The operating elements can concern for example markings or profiled raised portions of the encapsulation which characterize these as operating elements. The advantage is simpler operability for the wearer of the heating device.

In a further variant, the at least two contact elements disposed on the inside of the encapsulation have conductive material, e.g. conductive plastic material. If the disposed contact elements are in an inoperative position, these are at a spacing relative to the contact elements of the circuit board. In an operative position, the contact elements of the encapsulation touch the contact elements of the circuit board and thus close an electrical circuit. As a result of the fact that the contact elements of the encapsulation consist of conductive plastic material, these can, on the one hand, close the electrical circuit and, on the other hand, are compressible and pressure-insensitive, which ensure an improved lifespan of the control panel and of the electronics situated on the circuit board.

In a further variant, the at least two contact elements configured on the circuit board have respectively two strip conductors which are at a spacing from each other and engage in each other preferably like a comb. In this way, a large contact area for the contact elements of the inside of the encapsulation is formed so that a more robust mode of operation of the switch is ensured.

In a further variant, a time control means is added to the control circuit, the time control means detecting at least respectively a time duration of actuation of the at least two switches. It can be ensured by means of the time control means that accidental actuations of the switches do not lead to a change in temperature of the heat transfer elements. Accidental actuations of the switches are for example not uncommon in sport. The time control means measures the time over which a switch is closed or pressed and only after a time established within the time control means is a signal emitted to the control circuit that a change in the controlled temperature is intended to be initiated. The same applies for example for switching the heating device on and off. Over a further time interval which is preferably longer than the time interval of a change in temperature, it can be provided here that the control circuit switches the heating device off or on.

In a further variant, a display element is disposed on the circuit board and the encapsulation in the region of the display element is transparent so that a display of the display element is visible outwith the encapsulation for the wearer of the heating device. Via the display element, a wearer or operator of the heating device can detect what temperature setting is set at present. Upon a change in temperature due to operation of the operating element, the display changes correspondingly. The display is thereby visible in the region of the display element because of the transparency of the encapsulation, however it is protected from the effects of soiling and foreign bodies because of the encapsulation.

The above-mentioned variants of the heating device can be combined with each other in any manner.

In one variant of the glove, the latter has at least one pocket, the pocket being configured for receiving at least one, preferably rechargeable, battery and the terminal being guided from the encapsulation to the pocket within the outer casing. The terminal hence extends on the inside of the outer casing and can in addition be sewn together with the latter. In the pocket, merely the terminal and a short connection is left uncovered so that a certain flexibility is present in the movement of the terminal. The pocket can thereby be accommodated in the region of the wrist.

A variant of the pocket is characterized in that the pocket can be closed by a water-tight zip and preferably has at least two separately closable compartments. In the two pockets which can be closed preferably with a Velcro fastener, respectively one battery can be introduced. This is connected to the terminal of the heating device via a battery terminal, the terminals being protected from moisture with the help of the water-tight zip. When a battery is changed, the zip can be opened and, after opening of the pockets, the batteries can be removed and disposed of or recharged. Furthermore, this has the advantage that the heating device is fitted essentially without change within the glove and merely the batteries need be moved. This also increases the lifespan of the glove.

Such a glove is preferably produced in that firstly the heating device is produced. Subsequently, the flange-like edge of the encapsulation is connected to a back of the hand part of the outer casing. This can take place either by means of gluing or sewing, the back of the hand part hereby being able to have a recess for the operating element or being able to be without seams. Subsequently, the at least one heat transfer element is disposed in at least one pocket situated in one of the fingers of a glove in front of an inside of the outer casing. Furthermore, the terminal is installed in the direction of the wrist. Subsequent to these steps, the back of the hand part is sewn together with the remaining outer casing of the glove. At this time, the heating device is however already correctly positioned in the inner glove or the outer casing of the glove.

A heating device and a garment, for example a glove with a heating device, are intended to be explained in more detail with reference to some embodiments. There are shown:

DETAILED DESCRIPTION

Figure 1:
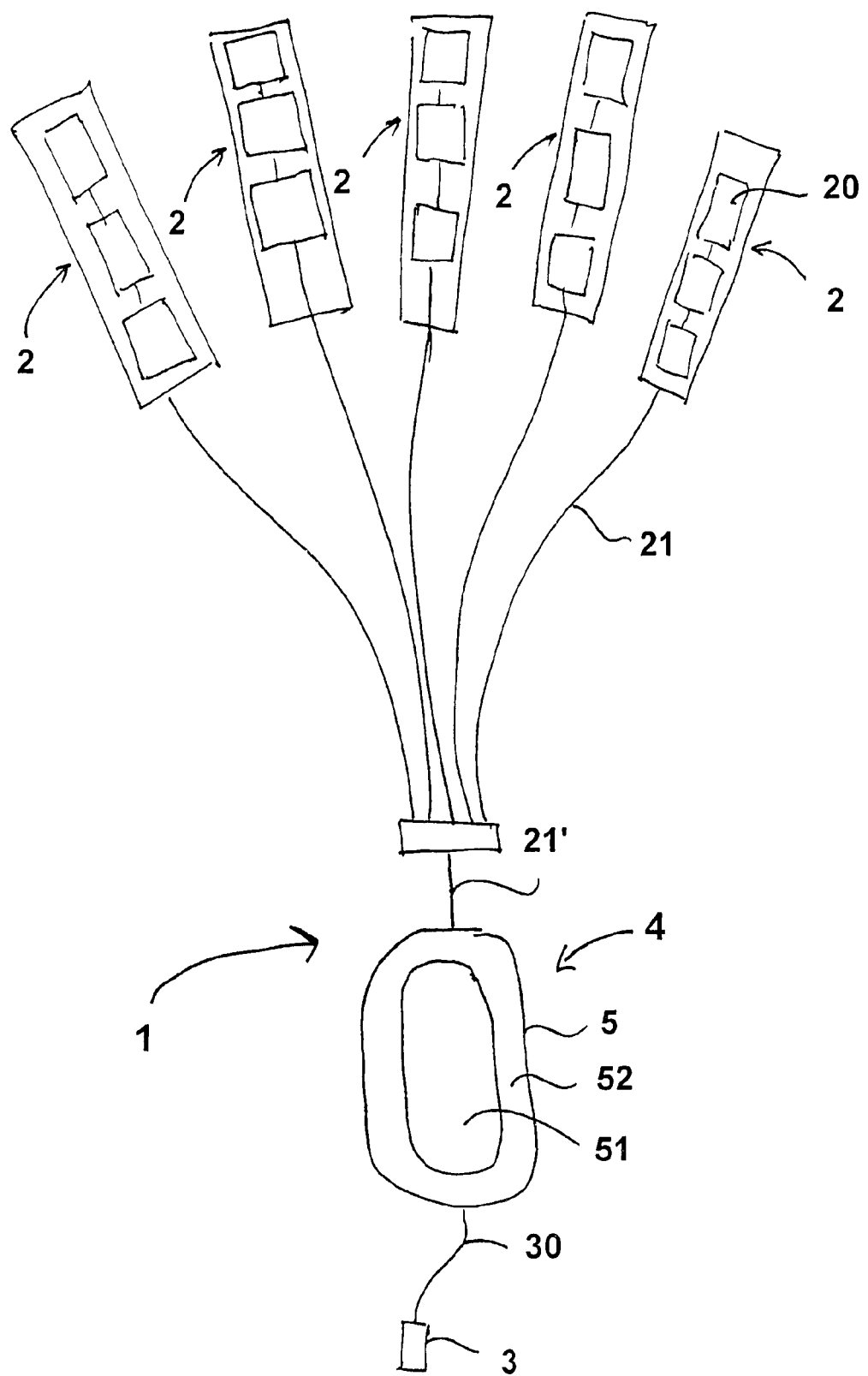
FIG. 1 illustrates a heating device according to one embodiment of the invention.

FIG. 1 shows a heating device 1 with five heat transfer elements 2, these respectively having at least one electrical heating element 20. Each heat transfer element 2 has a connection 21 which is connected to a common connection 21'. The connections are hereby configured via electrically conducting cables to an insulation layer. Furthermore a terminal 3 for an energy supply device is present, which device likewise has a connection 30 in the form of a cable. Both the connection 21' and the connection 30 run into the control panel 4 in which, in FIG. 1, merely the encapsulation 5 with the protruding flange-like edge 52 and the indicated chamber 51 is shown. The encapsulation 5 and the circuit board situated therein are dealt with in more detail in the subsequent Figures.

Figure 2:
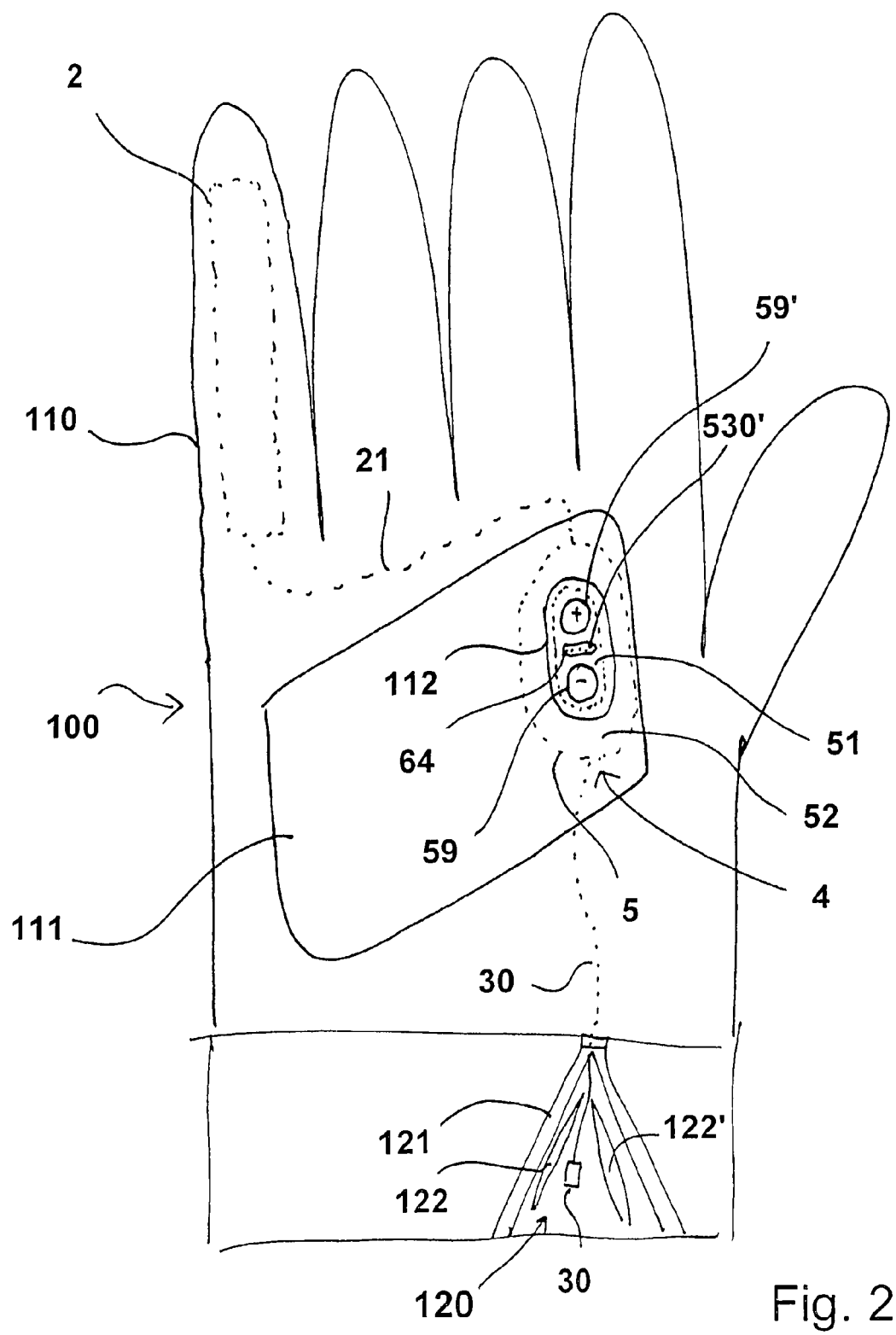
FIG. 2 illustrates a glove with a heating device according to one embodiment of the invention.

In FIG. 2, a glove 100 for a left hand is shown, in which glove a variant of the heating device 1 is integrated. The glove 100 has an outer casing 110, a part of the outer casing 110 being formed by the back of the hand part 111. The operating part 4 is recessed in the back of the hand part 111. The hatched lines thereby indicate that the features characterised therewith extend within the outer casing 110, i.e. are not visible from outside for an observer—apart from when there is a transparent outer casing. The operating part 4 is connected to the back of the hand part 111 by a seam 112. The seam thereby extends in the flange-like edge 52 of the illustrated encapsulation 5. The seams hence extend around the circuit board introduced in the chamber 51 and do not touch this. For a wearer of the glove 100, merely the operating elements 59, 59' and the display panel 64 are visible from the control panel 4 since the encapsulation 5 in the region 530' has a transparent configuration. The surface of the control panel which extends within the seam 112 is designed to be opaque apart from the transparent region 530'.

The glove 100 has in addition a pocket 120 with a watertight zip 121. Two compartments 122, 122' are disposed in the pocket 120, these being able to be at least partially closed with a Velcro fastener. Furthermore, the terminal 30 which is connected to the control panel 4 via the connection 30 is visible.

A battery is connected by plugging in via a battery terminal to the terminal 30 and supplies the control panel and the heat transfer elements with current. The zip 121 is closed so that the battery and the terminal 30 are protected. In the case where a rechargeable battery is used, such as for example a lithium ion accumulator, the zip 121 is opened, the battery terminal is separated from the terminal 30 and the battery terminal is connected to a charging device, the charging state being indicated on a charging device. In the case of the connection between the terminal 30 and the battery terminal, it is advantageous if the terminals can be connected non-interchangeably in order to avoid incorrect polarity. The non-interchangeability can thereby be achieved via plastic rails disposed on the terminal 30 and on the battery terminal.

Figure 3:
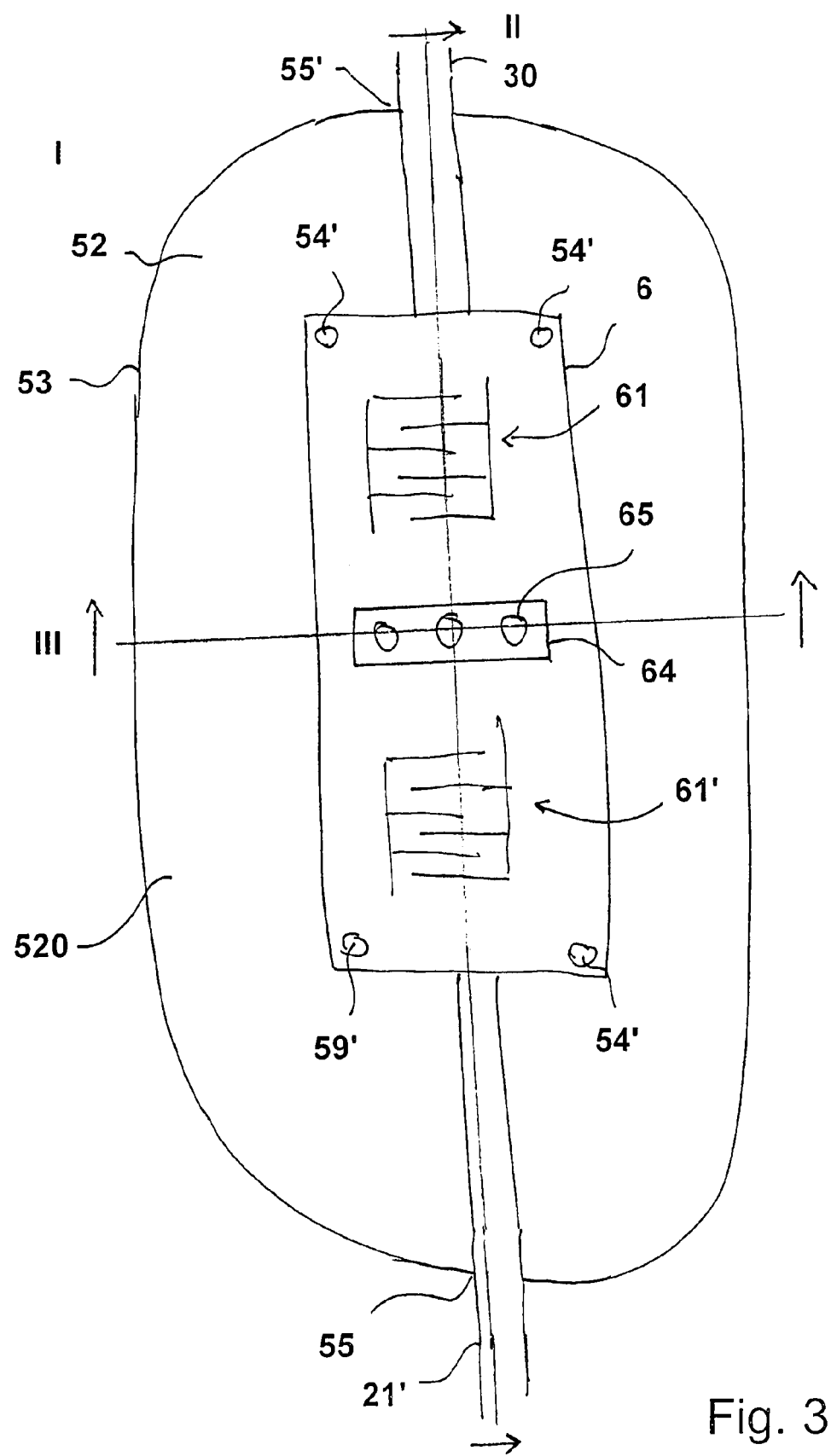
FIG. 3 illustrates a longitudinal section through the control panel of a heating device.

The control panel 4 is shown in FIG. 3, the encapsulation 5 which is visible for example in FIG. 1, being opened up in the drawing plane. The plane is called section I. A lower part 53 of the encapsulation 5 is shown, in the case of which the flange-like edge 52 of the lower part is visible and the chamber 51 is covered by the circuit board 6. On the edge 520 of the lower half, the connection 30 and the connection 21' are shown, as these were shown in FIG. 1. Support elements 54 which are explained in more detail in the subsequent Figures are shown in addition on the circuit board 6.

The circuit board 6 is a double-sided circuit board with strip conductors and electrical or electronic components on both sides of the circuit board. Contact elements 61, 61' and also a display panel 64 are shown on the side illustrated here. The contact elements 61, 61' thereby have two strip conductors at a spacing from each other, the strip conductors engaging respectively in each other like a comb and being at a spacing from each other. The display element 64 has three lighting elements 65, the display element 64 being connected to a control circuit. As a function of the control which is set, respectively one, two, three or none of the lighting elements 65 are illuminated and hence display the adjusted control stage of the heating device or the switched-on or switched-off status thereof. For example single or multicoloured LEDs are suitable as lighting elements.

Figure 4A:
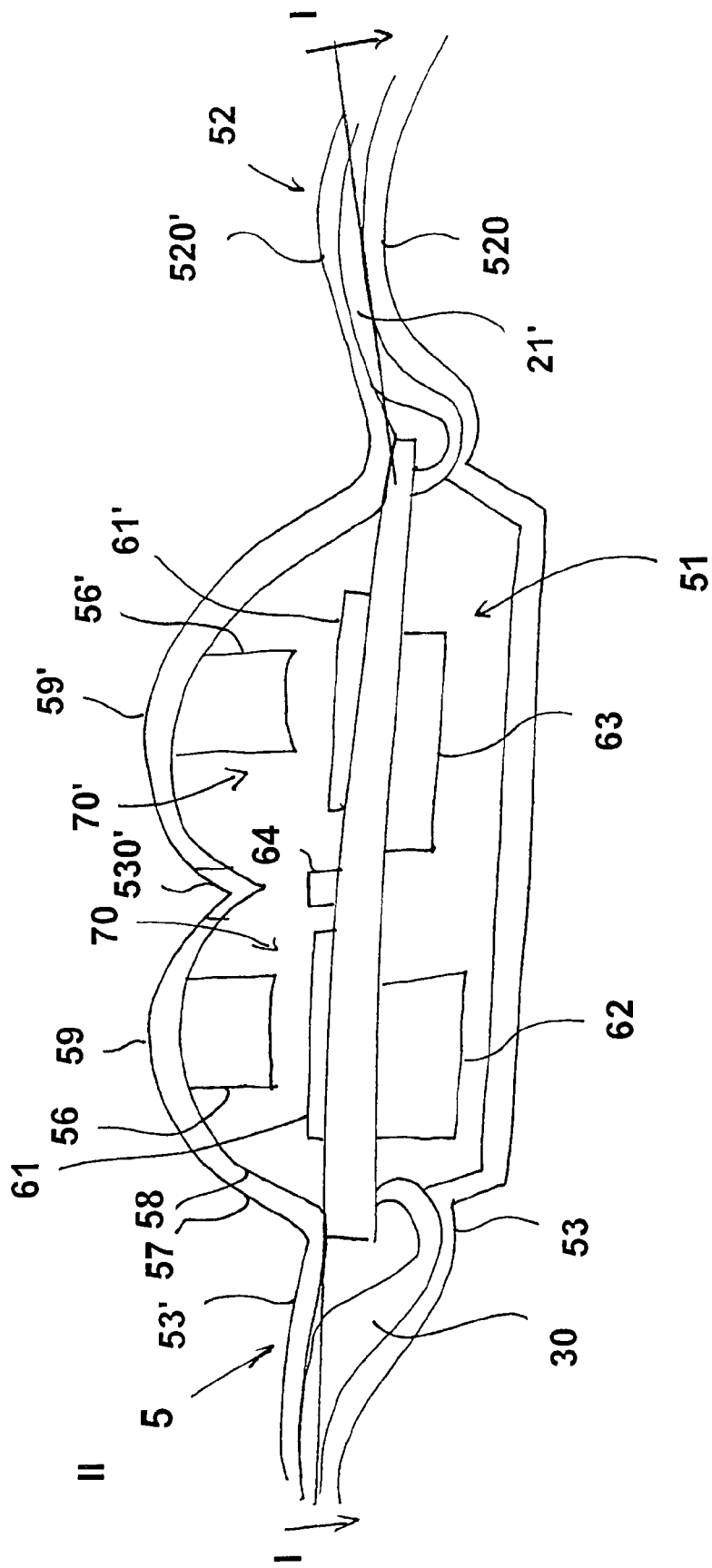
FIGS. 4a and 4b illustrate cross-sections through the heating device shown in FIG. 3.

In FIG. 4a, the control panel 4 shown in FIG. 3 is shown in section II. It can be clearly detected that the lower part 53 in conjunction with the upper part 53' form a closed encapsulation 5 for the circuit board 6. Merely openings for the connections 21' and 30 are thereby present, which extend through between the edge 520 of the lower part and the edge 520' of the upper part. The connection 21' has, between the edge 520 and the edge 520', a thickness of approx 2 mm. The lower part 53 and also the upper part 53' have a thickness between 1 and 3 mm. Furthermore, the course of the section plane I is illustrated.

The connections 21' and 30 are connected to the circuit board 6. On the side of the circuit board orientated towards the upper part 53', contact elements 61, 61' and also the display panel 64 are applied. Furthermore, the operating elements 59, 59' which are produced by dome-like convexities are shown on the outside 57 of the upper part 53'. The operating elements 59, 59' are situated above the switches 70, 70' which have the contact elements 56, 56' and the contact elements 61, 61'. Contact elements 56, 56' are fitted on the inside 58 of the encapsulation, said contact elements consisting of a conductive plastic material on the surface orientated towards the contact elements 61, 61'. Since the surface in the inoperative position shown in FIG. 4a is at a spacing from the contact elements 61, 61', a change of state of the control circuit 62 can only take place when the contact elements 56 or 56' touch the contact elements 61, 61' and hence connect the strip conductors, which engage in each other like a comb, in an electrically conducting manner.

On the underside of the circuit board, an electronic control circuit 62 and a time control means 63 are shown. The time control means 63 hereby measures the duration of the contact between the contact elements 56 or 56' and contact elements 61 or 61' and passes on the information that the switches 70 or 70' are closed to the control circuit only when the latter have been closed for a time interval T. A period of time for the interval T of 1 to 2 seconds hereby suffices for the interval T. Furthermore, the time control means transmits a further command to the electronic control means when the switch 70 or 70' is closed for longer than 2 to 5 seconds. By means of this command, the electronic control circuit 62 switches the heat transfer elements 2 off.

Furthermore, the transparent region 530' of the upper part 52' is illustrated, through which the display present on the display panel 64 is visible for an observer of the control panel.

It can be detected clearly in the illustration of FIG. 4a how the chamber 51 formed between the upper part 53' and the lower part 53 is configured such that, in the normal case, the electronic components, such as for example the electronic control circuit 62, the time control means 63 and also the contact elements 61, 61' and the display panel 64 are not touched by the encapsulation 5.

Figure 4B:
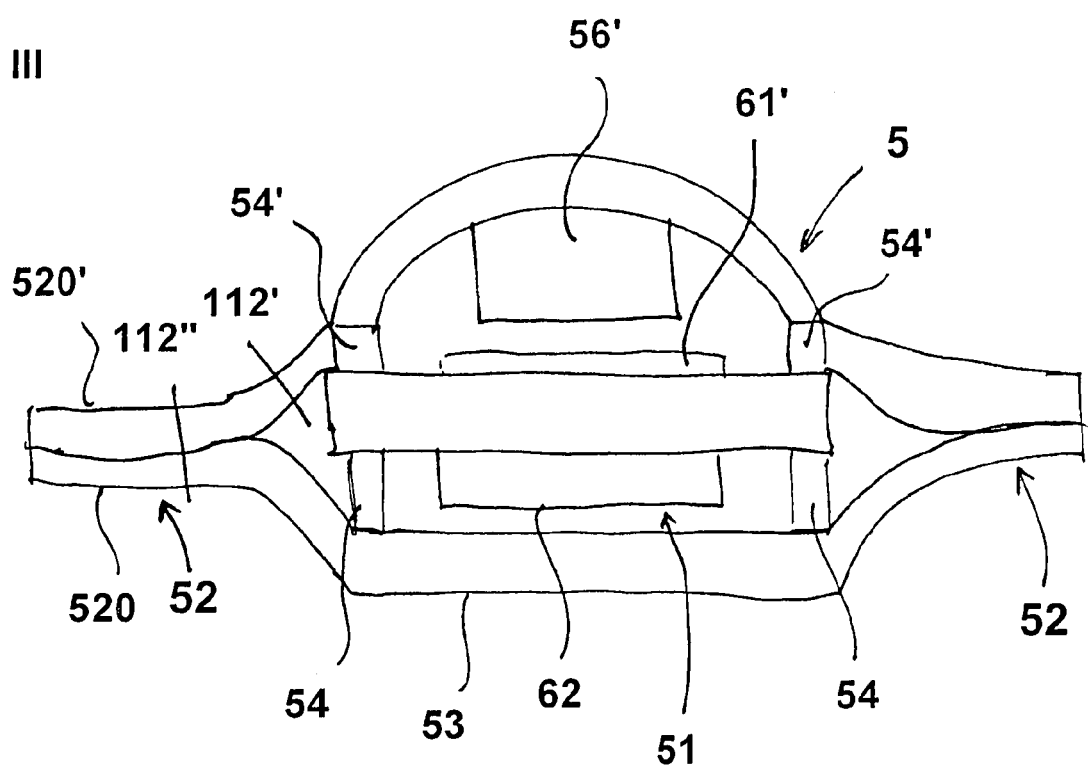

In FIG. 4b, the section III through the control panel 4 shown in FIG. 3 is shown. It can be detected clearly how the edge 520 of the lower part 52 and the edge 520' of the upper part 53' are situated one upon the other without a gap. The edges 520 and 520' are thereby glued to each other and thus form the closed capsule. In FIG. 4b, the support elements 54 and the support elements 54' can be detected clearly. They serve as spacers and form additional stabilization of the chamber 51 so that, even when a pressure is applied to the lower part 53, the electrical components, such as for example the control circuit 62, are also supported in addition, at least partially. The same applies to the support elements 54' of the upper part 53', contacting between the contact elements 56' and 61' being desired here.

Furthermore, two possible positions for sewing to the back of the hand part of a glove are illustrated. This relates, on the one hand, to the position 112' which passes merely through the upper part of the encapsulation 5 and the back of the hand part is sewn merely to the upper part 53' and also, on the other hand, the position 112" in which sewing both by the upper part 53' and the lower part 53 takes place.

The flange-like edge can have a width of 3 mm to 2 cm, preferably of 5 mm to 1.2 cm.

Various features and advantages of the invention are set forth in the following claims.

The invention claimed is:

1. Garment having an outer casing and a heating device which is connected to the outer casing and is configured in particular for heating and/or temperature-control of a skin surface with deep effect on partial regions of a human body, the garment comprising:
   at least one heat transfer element,
   at least one terminal for an energy supply device,
   at least one control panel with an encapsulation,
   at least one circuit board with an electric control circuit for controlling the temperature of the heat transfer element and
   at least two switches for manual adjustment of the temperature, the circuit board being connected to the at least one heat transfer element and to the at least one terminal,
   wherein the encapsulation includes a flexible material and has a chamber receiving the circuit board and a flange-like edge surrounding the chamber, the chamber and the edge including the flexible material, and each of the at least two switches is formed by at least one contact element which is disposed on an inside of the encapsulation and by at least one contact element which is configured on the circuit board, and the flange-like edge is connected to the outer casing.

2. Garment according to claim 1, wherein the flexible material is silicone.

3. Garment according to claim 1, wherein the encapsulation comprises an upper and a lower part, the chamber being formed between the upper and lower part and the upper and the lower part being connected to each other at their edge and forming the edge of the encapsulation.

4. Garment according to claim 1, wherein the encapsulation has at least one opening for guiding through a connection between the circuit board and at least one of the at least one heat transfer element and/or the at least one terminal.

5. Garment according to claim 1, wherein operating elements are disposed on the outside of the encapsulation, which operating elements are situated above the contact elements which are disposed on the inside of the encapsulation so that a pressure applied on one of the two operating elements actuates the switch situated thereunder.

6. Garment according to claim 1, wherein the contact elements disposed on the inside of the encapsulation comprise conductive material.

7. Garment according to claim 1, wherein a display element is disposed on the circuit board and the encapsulation in the region of the display element is transparent so that a display of the display element is visible outwith the encapsulation.

8. Garment according to claim 1, wherein the garment is a glove.

9. Garment according to claim 8, wherein at least one pocket is present and the pocket is configured for receiving at least one battery and the terminal is guided from the encapsulation to the pocket.

10. Heating device for a garment having an outer casing, in particular for heating and temperature-control of at least one partial region of a human body, comprising at least one heat transfer element, at least one terminal for an energy supply device, at least one control panel with an encapsulation, at least one circuit board with an electrical control circuit for controlling the temperature of the heat transfer element and at least one switch for manual adjustment of the temperature, and the circuit board is connected to the at least one heat transfer element and to the at least one terminal, wherein the encapsulation consists of plastic material and has a chamber receiving the circuit board and a flange-like edge surrounding the chamber, the edge consisting of a flexible material, and the at least one switch is formed by at least one contact element which is disposed on an inside of the encapsulation and by at least one contact element which is configured on the circuit board, and the flange-like edge is able to be connected to the outer casing of the garment.

11. Heating device according to claim 10, wherein the plastic material comprises at least one of silicone, rubber, and PE.

12. Garment according to claim 1, wherein the flange-like edge is sewn or glued to the outer casing.

13. A garment comprising:
   an outer layer of fabric and an inner layer of fabric; and
   a heating device connected to the outer layer of the fabric, the heating device including
      a heat transfer element positioned between the outer layer of fabric and the inner layer of fabric,
      a terminal for connection to an energy supply device,
      a control circuit in electrical communication with the heat transfer element and the terminal, the control circuit operable to control the temperature of the heat transfer element, and
      a housing having a first layer of a flexible material and a second layer of flexible material and forming a chamber therebetween configured to support the control circuit, and
   wherein the first layer of the flexible material is connected to an underside surface of the outer layer of the fabric, and wherein a portion of the first layer of the flexible material is at least partially exposed through an opening in the outer layer of the fabric.

14. The garment of claim 13 wherein the first layer of the flexible material and the second layer of the flexible material are configured to receive a plurality of stitches to secure the housing to the outer layer of the fabric.

15. The garment of claim 14 wherein the plurality of stitches form a seam around the control circuit.

16. The garment of claim 13 wherein the first layer of the flexible material is fused to the underside surface of the outer layer of the fabric.

17. The garment of claim 13 wherein the heating device further includes a control panel having a first switch for controlling the temperature of the heat transfer element.

18. The garment of claim 17 wherein the control panel includes a second switch for controlling the temperature of the heat transfer element.

19. The garment of claim 18 wherein the heating device includes a display panel positioned between the first switch and the second switch.

20. The garment of claim 17 wherein the control panel is formed within the first layer of the flexible material.

21. The garment of claim 13 wherein the heating device further includes a control panel having a first contact element connected to an underside surface of the first layer of the flexible material.

22. The garment of claim 21 wherein the first contact element is configured to contact a second contact element on the control circuit, and wherein the first contact element makes contact with the second contact element when a user presses the control panel to adjust the temperature of the heat transfer element.

23. The garment of claim 22 wherein the control panel further includes a third contact element connected to an underside surface of the first layer of the flexible material.

24. The garment of claim 23 wherein the third contact element is configured to contact a fourth contact element on the control circuit, and wherein the third contact element makes contact with the fourth contact element when a user presses the control panel to adjust the temperature of the heat transfer element.

25. The garment of claim 1 further comprising a display panel positioned between the two switches.

26. The garment of claim 1 wherein an upper surface of the encapsulation is connected to an underside surface of the outer casing of the garment.

27. The garment of claim 1 wherein the garment further includes an inner casing, and wherein the flange-like edge is at least partially positioned between the inner casing and the outer casing of the garment.

28. The garment of claim 27 wherein an upper surface of the flange-like edge is connected to an underside surface of the outer casing of the garment.

29. The garment of claim 1 wherein the flange-like edge is configured to receive a plurality of stitches to form a seam at least partially around the circuit board.

* * * * *

UNITED STATES PATENT AND TRADEMARK OFFICE
CERTIFICATE OF CORRECTION

PATENT NO.        : 8,664,571 B2                                                  Page 1 of 1
APPLICATION NO. : 12/864456
DATED             : March 4, 2014
INVENTOR(S)       : Macher et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 591 days.

Signed and Sealed this

Twenty-ninth Day of September, 2015

Michelle K. Lee
*Director of the United States Patent and Trademark Office*